United States Patent
Mansour

(10) Patent No.: US 8,647,333 B2
(45) Date of Patent: Feb. 11, 2014

(54) OPHTHALMIC SURGICAL DEVICE

(75) Inventor: Fouad Mansour, Sandy Springs, GA (US)

(73) Assignee: Cygnus LLC, Roswell, GA (US)

( * ) Notice: Subject to any disclaimer, the term of this patent is extended or adjusted under 35 U.S.C. 154(b) by 1524 days.

(21) Appl. No.: 11/934,761

(22) Filed: Nov. 3, 2007

(65) Prior Publication Data

US 2009/0118715 A1    May 7, 2009

(51) Int. Cl.
*A61F 9/008* (2006.01)
*A61B 18/20* (2006.01)

(52) U.S. Cl.
USPC .......................................... 606/4; 250/227.24

(58) Field of Classification Search
USPC ..................................................... 250/227.24
See application file for complete search history.

(56) References Cited

U.S. PATENT DOCUMENTS

| | | | |
|---|---|---|---|
| 4,029,391 A * | 6/1977 | French ............................. | 385/31 |
| 5,275,593 A | 1/1994 | Easley et al. | |
| 5,323,766 A | 6/1994 | Uram | |
| 5,722,970 A | 3/1998 | Colvard et al. | |
| 5,891,022 A * | 4/1999 | Pologe ......................... | 600/323 |
| 6,110,195 A * | 8/2000 | Xie et al. ......................... | 607/89 |
| 7,189,226 B2 | 3/2007 | Auld et al. | |
| 2007/0100401 A1* | 5/2007 | Lin ................................. | 607/89 |
| 2007/0265602 A1* | 11/2007 | Mordaunt et al. ................ | 606/4 |
| 2008/0262442 A1* | 10/2008 | Carlin et al. ................... | 604/264 |

FOREIGN PATENT DOCUMENTS

WO  PCT/US2008/078137    9/2008

OTHER PUBLICATIONS

Lori Baker Schena, Vitrectomy and the Vanishing Suture, Eye Net, Mar. 2003, 28-31, American Academy of Ophthalmology.

* cited by examiner

*Primary Examiner* — Sam Yao
*Assistant Examiner* — Scott T Luan
(74) *Attorney, Agent, or Firm* — Baker & Hostetler LLP

(57) ABSTRACT

An ophthalmic surgical device is disclosed that combines laser energy for treatment of vision or ocular defect and illumination energy for visualization of a treatment site during surgery in a single common waveguide fiber, thereby enabling reduction of a diameter of a probe or canula of the device, whereby a smaller incision may be utilized to reduce trauma to the eye. The device may further include additional features, such as a conduit for supply of material or removal of material from the treatment site.

16 Claims, 3 Drawing Sheets

OPHTHALMIC SURGICAL DEVICE

TECHNICAL FIELD

The present invention relates generally to ocular surgery devices, and, more particularly, to a waveguide ophthalmic surgery probe.

BACKGROUND OF THE INVENTION

Laser energy has been implemented for use with surgical devices in treatment of various kinds of vision or ocular defects. In many such implementations, an incision or other opening into eye of the patient is required to accurately deliver the laser energy to the treatment site, such as a retina. Furthermore, one or more additional surgical tool(s), such as a surgical-site visualization tool, may be needed. Such additional surgical tools may require additional incisions, whereby recovery time for the patient may be increased, and wherein the risk of complications may likewise be increased.

In an attempt to reduce the need for such additional tools, particularly those requiring a separate incision, laser energy surgical probes have been designed to deliver both laser energy for treatment and illumination energy, such as for visualization, using a single probe. Thus, only a single incision may be required for visualization of the treatment area, as well as for delivery of laser energy to the treatment area to accomplish the surgery.

Such devices fail, however, to reduce the need for additional incisions for other additional surgical instruments, and further disadvantageously require a relatively large incision, and associated sutures, due to the necessity for separate conduits for laser and visualization energy. As such, it is clear that there is an unmet need for an ophthalmic surgical device capable of delivering illumination energy and laser energy for treatment of a patient's eye via a single incision, while maintaining a small diameter probe for reducing unwanted injury to the eye.

BRIEF SUMMARY OF THE INVENTION

Briefly described, in a preferred embodiment, the present invention overcomes the above-mentioned disadvantages and meets the recognized need for such a device by providing an ophthalmic surgical device that combines laser energy and illumination energy within a single-fiber waveguide housed within a surgical probe, whereby laser and illumination energy may selectively be delivered, via a single small incision, to a surgical site for use in treatment of vision and/or ocular defects or problems via a single small incision.

According to its major aspects, and broadly stated, the surgical device includes a hollow probe having a single-fiber waveguide disposed therein and suitable for conducting laser energy and illumination energy therealong. The single-fiber waveguide may be coupled to a laser energy source and to an illumination energy source, wherein the single fiber waveguide combines the energy from each source for common delivery thereof to the surgical site.

More specifically, the surgical device comprises a handpiece adapted for manipulation by a user, such as a surgeon, and a probe attached thereto. During surgery, the user may control the position, attitude, location, or the like, of the probe via manipulation of the hand-piece, whereby a tip at a first end of the probe may be controlled. A source of laser energy is provided and is operable with the probe and the hand-piece to supply laser energy to a second end of the probe, such as via one or more fiber waveguide(s). An optical coupling is preferably provided to ensure adequate transmission of the laser energy from the laser energy source into a first end of a single-fiber waveguide disposed within the probe.

Likewise, an illumination energy source is provided and is operable with the probe and the hand-piece to supply illumination energy (and received reflected visualization energy, such as when in use with a microscope) to the second end of the probe, such as via one or more different fiber waveguide(s). The optical coupling preferably further ensures adequate transmission of the illumination energy from the illumination energy source into the first end of the single-fiber waveguide of the probe. The single-fiber waveguide preferably conducts the laser and/or illumination energies to a second end of the single-fiber waveguide, proximate the tip of the probe, where the energies may exit the probe for treatment and/or visualization of the treatment site.

In its simplest form, the optical coupling comprises at least a portion of a cross-sectional surface of the single-fiber waveguide disposed in abutting contact with at least a portion of a cross-sectional surface of a laser energy source waveguide, and at least another portion of the cross-sectional surface of the single-fiber waveguide disposed in abutting contact with at least a portion of a cross-sectional surface of an illumination energy source waveguide. The optical coupling is preferably adequately efficient to allow a relatively low-power laser energy source and a relatively low-power illumination energy source to be utilized, while still allowing transmission of sufficient amounts of each energy into and through the single-fiber waveguide. Alternatively, however, the optical coupling may comprise one or more reflective device(s), refractive device(s), anti-reflective coating(s), anti-scattering coating(s), optical gel(s), tapered fiber(s), fusion, bond(s), weld(s), combinations thereof, or the like, to reduce losses during transmission of one or both of the laser energy and the illumination energy from the respective source to the first end of the single-fiber waveguide.

The probe is preferably formed as a generally hollow cylinder or tube, wherein the single-fiber waveguide may be carried. The probe may comprise a durable material, such as a metal, plastic, ceramic, or the like, whereby the single-fiber waveguide may be protected from damage, including cuts, scratches, abrasion, or the like, which damage may adversely impact performance of the single-fiber waveguide during use. A space between the single-fiber waveguide and the cylinder or tube may be used for removal of waste or fluid material, for supply of material, such as a medicine, a rinsing agent, or the like, or for detecting and/or measuring one or more parameter proximate the surgical site. Alternatively, an additional conduit may be included within the hollow center of the probe, for removal or supply of a selected material and/or measuring one or more parameter.

Accordingly, one feature and advantage of the present invention is its ability to deliver laser energy and illumination energy through a single-fiber waveguide, whereby a necessary dimension of an incision, or a required number of incisions, may be reduced through the elimination of duplicative fiber waveguides via effective and efficient combination of each of the laser energy and the illumination energy within the single-fiber waveguide.

Another feature and advantage of the present invention is its ability to combine and transmit light energy in a probe of a surgical instrument via a single-fiber waveguide, wherein the light energy is supplied from two or more separate conventional sources of light energy, thereby eliminating the need to replace, modify, or supplement pre-existing light energy source devices.

These and other features and advantages of the present invention will become more apparent to those ordinarily skilled in the art after reading the following Detailed Description of the Invention and Claims in light of the accompanying drawing Figures.

BRIEF DESCRIPTION OF THE DRAWINGS

Accordingly, the present invention will be understood best through consideration of, and with reference to, the following drawing Figures, viewed in conjunction with the Detailed Description of the Invention referring thereto, in which like reference numbers throughout the various Figures designate like structure, and in which.

Figure 1:
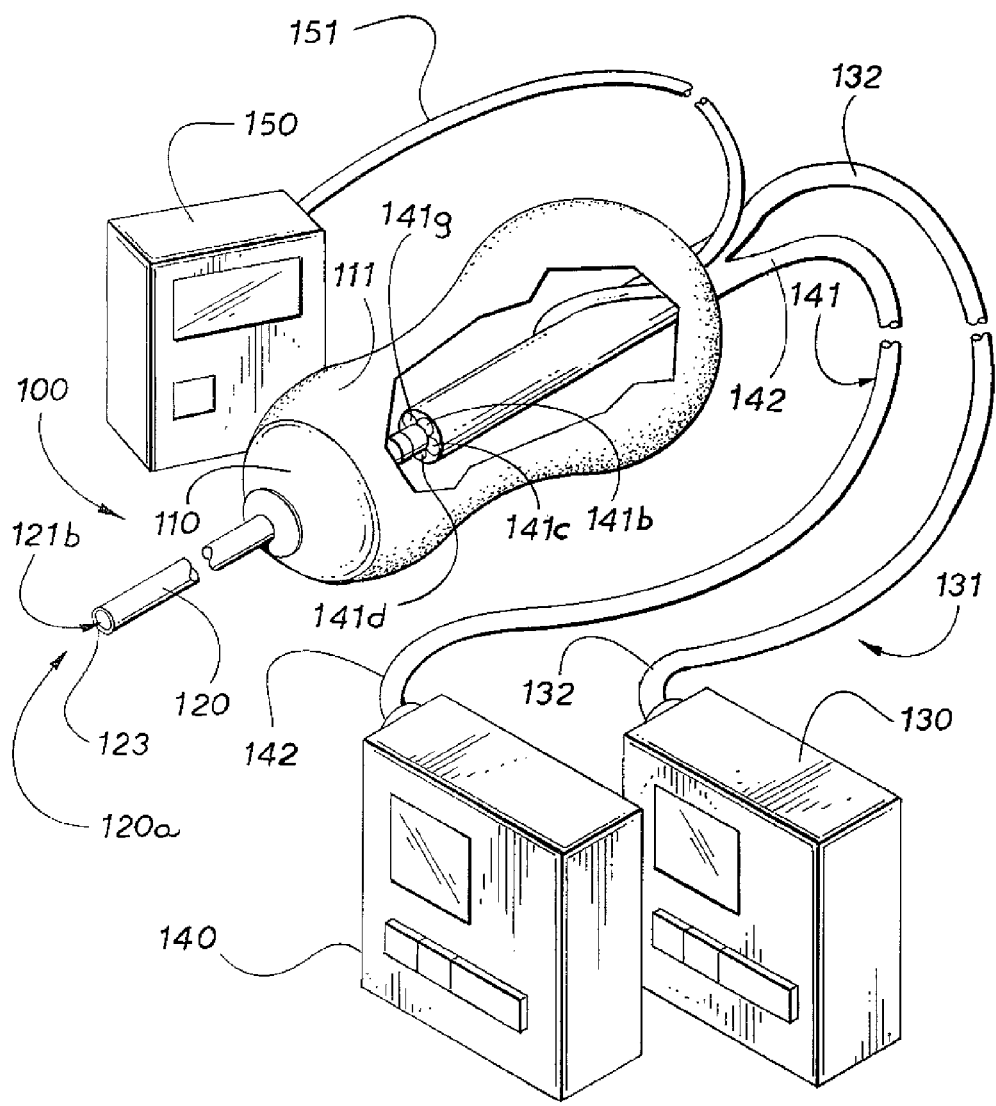
FIG. 1 is a partial cut-away perspective view of an ophthalmic surgical device according to the present invention.

It is to be noted that the drawings presented are intended solely for the purpose of illustration and that they are, therefore, neither desired nor intended to limit the invention to any or all of the exact details of construction shown, except insofar as they may be deemed essential to the claimed invention.

DETAILED DESCRIPTION OF THE INVENTION

In describing preferred embodiments of the present invention illustrated in the figures, specific terminology is employed for the sake of clarity. The invention, however, is not intended to be limited to the specific terminology so selected, and it is to be understood that each specific element includes all technical equivalents that operate in a similar manner to accomplish a similar purpose.

In that form of the preferred embodiment of the present invention chosen for purposes of illustration, FIGS. 1-4 show instrument 100 comprising hand-piece 110 and probe or canula 120, in combination with laser energy source 130, illumination energy source 140, and accessory 150. Each of laser energy source 130 and illumination energy source 140 is preferably formed as a currently-available energy source device adapted to supply appropriate respective laser and illumination energies via respective source fiber waveguides 131 and 141, such as a single-fiber waveguide or a multi-fiber waveguide. Accordingly, each of laser energy source 130 and illumination energy source 140 is preferably controllable to selectively adjust an intensity, a wavelength/frequency, a polarity, or other characteristic of the energy, including selectively preventing any output thereof. It is contemplated, however, that other light sources may be used, as desired, to provide a light having a desired wavelength/frequency, including those within the visible spectrum, as well as those outside the visible spectrum.

Specifically, laser energy source waveguide 131 is preferably formed as single-fiber waveguide 131a, whereas illumination energy source waveguide 141 is preferably formed as a multi-fiber waveguide, such as six fiber waveguides 141b-g. As is known in the art, each of waveguides 131 and 141 may include durable covers 132 and 142 to prevent damage to the waveguide. Each of source waveguides 131 and 141 may additionally include an appropriate connector at a proximal end for enabling removable connection of the waveguide to a respective energy source device.

Hand-piece 110 preferably includes grip 111, whereby a user, such as a surgeon, may grasp and manipulate instrument 100 to control a position, attitude, and/or orientation of probe 120 as desired, and probe 120 mounted proximate a distal end thereof. Probe 120 is preferably formed as generally hollow tube 125, such as a round cylinder, having a generally small exterior diameter, such as approximately 25 gauge, approximately 23 gauge, or the like, suitable for use with a trocar, and formed from a substantially durable material, such as a surgical-grade metal, plastic, ceramic, or the like, e.g. stainless steel.

Single-fiber waveguide 121 is preferably disposed within tube 125 and preferably has a cross-sectional area less than that of a hollow interior of tube 125, wherein a space between single-fiber waveguide 121 and tube 125 defines conduit 123, which may be used to provide access to distal end 120a, i.e. to the tip, of probe 120 for supply and/or removal of one or more selected material(s), or for detection or measurement of one or more selected parameter(s). When such a space is utilized, tube 125 may preferably include an opening through a sidewall thereof for allowing passage of material, whereby material may be diverted from tube 125 and not interfere with an interface To between single-fiber waveguide 121 and source fiber waveguides 131 and 141. Conduit 151 may be operable with such an opening to operably connect accessory 150 to the space between single-fiber waveguide 121 and tube 125.

By way of example, and not limitation, accessory 150 may be formed as a supply of wash or rinse fluid, a source of gas, a vacuum device for removal of waste or other substance from the surgical site, an energy source, such as an infrared energy source or the like, or one or more sensor(s) for detecting one or more parameters). As such, conduits 151 and 123 are preferably selected to provide adequate means of transmission, supply, removal, or the like, of one or more selected material(s), chemicals), energy(ies), parameter(s), or the like, without contamination, loss, degradation, or the like, of the selected materials), chemical(s), energy(ies), parameters, or the like.

Accordingly, selected material may be removed from, or supplied to, distal end 120a of probe 120 by accessory 150 via conduit 151 and conduit 123. Alternatively, one or more selected parameter(s) may be measured proximate distal end 120a of probe 120 via one or more sensor(s) disposed proximate distal end 120a of probe 120, or elsewhere within instrument 100, and one or more signal(s) corresponding to the parameter communicated to accessory 150 via conduits 123 and 151, or via a conductor or other signal carrier disposed therein. As another alternative, one or more sensor(s) may be included in accessory 150, and may measure one or more parameters) proximate hand-piece 110, probe 120, or proximate distal end 120a of probe 120, via conduits 151 and 123.

Single-fiber waveguide 121, disposed within tube 125, preferably extends from distal end 120a of probe 120 to optical coupling 115, proximate proximal end 120b thereof. Optical coupling 115 preferably defines an operable connection of single-fiber waveguide 121 and each of source waveguides 131 and 141. Such operable connection may be accomplished via an abutting relationship of at least a portion of proximal end 121a of single-fiber waveguide 121 with at least a portion of one or more fiber waveguide(s) of each of source waveguides 131 and 141. Each fiber waveguide of source waveguides 131 and 141 is preferably optically coupled to single-fiber waveguide 121 at proximal end 121a thereof, whereby laser energy and illumination energy may be transmitted into single-fiber waveguide 121.

Figure 2:
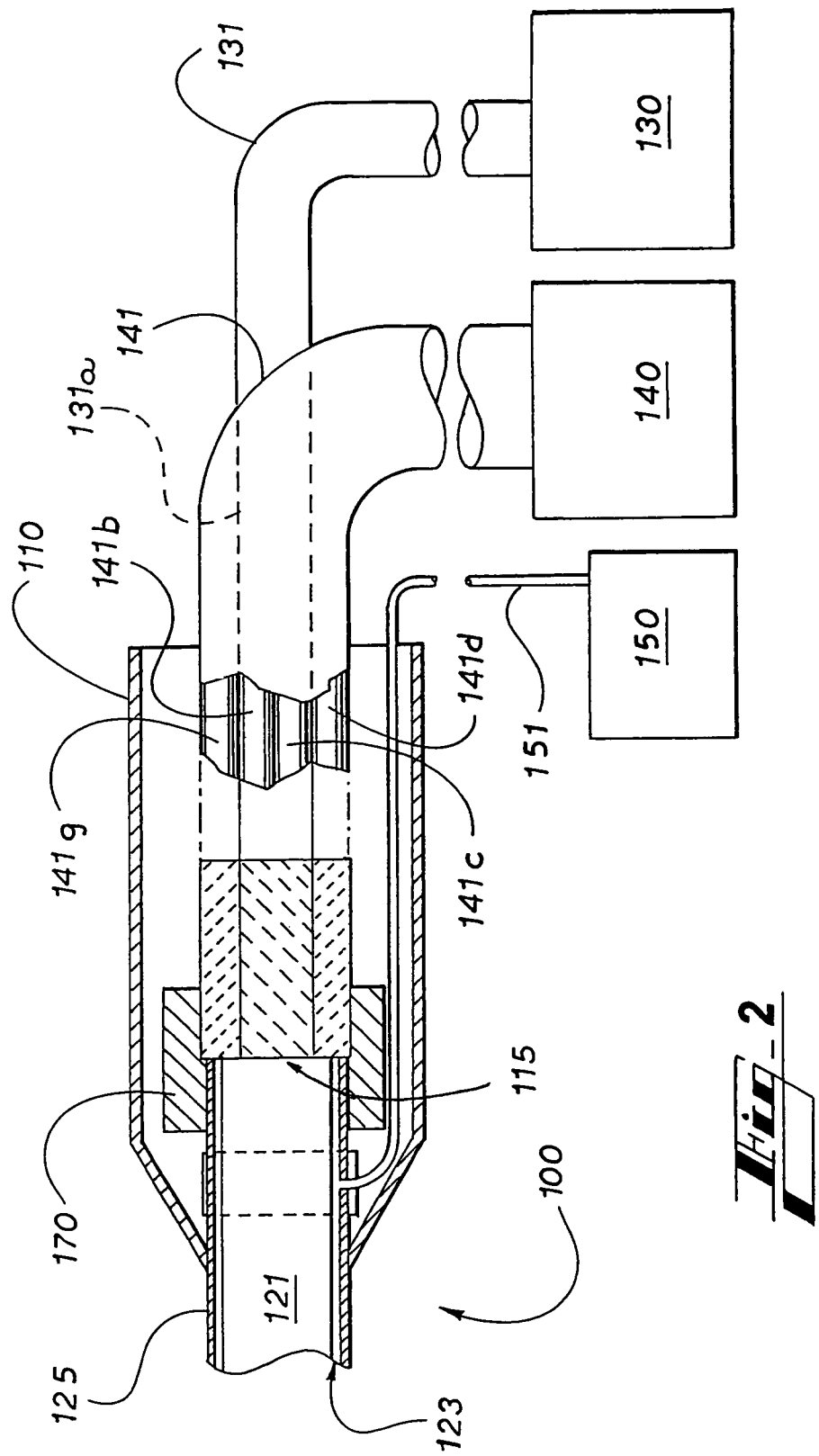
FIG. 2 is an axial-section view of the ophthalmic surgical device of FIG. 1.

According to the preferred embodiment, single-fiber waveguide 131a of source waveguide 131 is optically connected to single-fiber waveguide 121 of probe 120, such as proximate a cross-sectional center of single-fiber waveguide 121, via optical coupling 115. Further according to the preferred embodiment, each of the preferred plurality of six fiber waveguides 141b-g of source waveguide 141 is connected to single-fiber waveguide 121 of probe 120 via optical coupling 115. Each of fiber waveguides 141b-g is preferably disposed about single-fiber waveguide 131, as shown in FIG. 2. As will be understood by those ordinarily skilled in the art, a cross-sectional area of single-fiber waveguide 131 is preferably smaller than a cross-sectional area of single-fiber waveguide 121, and the total cross-sectional area of source waveguides 131 and 141, arranged as described above, may be greater than the cross-sectional area of single-fiber waveguide 121. Nonetheless, a sufficient amount of laser energy and of illumination energy is transmitted into single-fiber waveguide 121 via optical coupling 115.

Fiber waveguides 121, 131a, and 141b-g are preferably retained in such operable connection via coupler 170. Coupler 170 may be free to move within hand-piece 110, or may be connected to hand-piece 110, such as via a potting, an adhesive, a structural member, or the like. Fiber waveguides 131a and 141b-g, and probe 120 and/or single-fiber waveguide 121 are preferably retained within coupler 170 via friction fit, adhesive, potting, threading, or the like, and may or may not be removable therefrom. Coupler 170 preferably prevents optical coupling 115 from being adversely affected during manipulation of instrument 100, including when a tension force is applied to one or more of source waveguides 131 and 141, and conduit 151. Thus, coupler 170 preferably ensures that an adequate amount of light energy is transmitted between each of source waveguides 131, 141 and single-fiber waveguide 121.

In order to ensure that an adequate amount of laser and illumination energies are transmitted into single-fiber waveguide 121, one or more refractive device, reflective device, anti-reflective coating, anti-scattering coating, optical gel, tapered fiber, fusion bond, weld, combinations thereof, or the like, may be included in optical coupling 115, and may be retained in position via coupler 170. For example, referring more particularly to FIG. 3, lens 161 may be disposed in optical communication with each of the fiber waveguides of source waveguides 131 and 141 and single-fiber waveguide 121, whereby laser and illumination energy may be transferred therebetween, while reducing energy loss during such transfer. Selective arrangement and sizing of source waveguides 131 and 141 and single-fiber waveguide 121 may allow adequate transfer of laser and illumination energy for surgical use even though a portion of such energies may be lost at optical coupling 115 due to a difference in diameters of single-fiber waveguide 121 within probe 120 and the group of fiber waveguides of source waveguides 131 and 141. Optionally, lens 161, or other refractive device, reflective device, tapered fiber, optical gel, or the like, may be retained within coupler 170, or may be otherwise coupled to source waveguides 131, 141, and single-fiber waveguide 121 (and/or probe 120), such as via adhesive, fusion bond, weld, potting, or the like.

Figure 3:
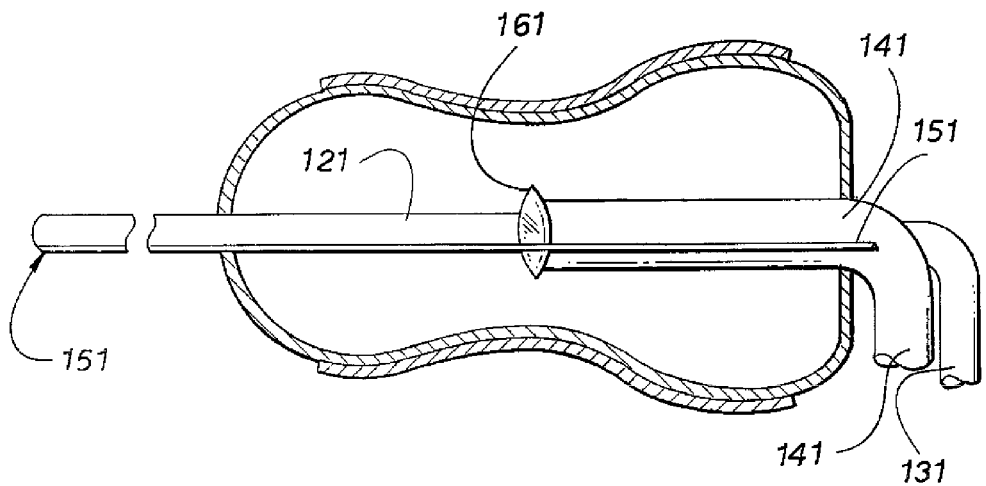
FIG. 3 is an axial-section view of an ophthalmic surgical device according to an alternate configuration.

With continued reference to FIG. 3, single-fiber waveguide 121 may optionally be securely housed within tube 125 of probe 120 via potting, adhesive, friction fit, or the like, wherein a space between single-fiber waveguide 121 and tube 125 is substantially reduced or eliminated, in order to reduce a dimension of probe 120. Preferably, an interior dimension of tube 125 of probe 120 may be reduced to a size substantially equal to a corresponding exterior dimension of single-fiber waveguide 121. In such a case, conduit 123 is effectively eliminated, and instrument 100 may not be operable with accessory 150. If, however, access for accessory 150 is desired, and potting, adhesive, or other filler is desired between tube 125 and single-fiber waveguide 121, then conduit 151, formed as a tube, may be included within probe 120 and may be connected to accessory 150 to provide access to distal end 120a of probe 120. In such an arrangement, conduit 151 is preferably arranged such that it does not interfere with transmission of light energy at optical coupling 115, but may, nonetheless, pass through optical coupling 115.

Figure 4:
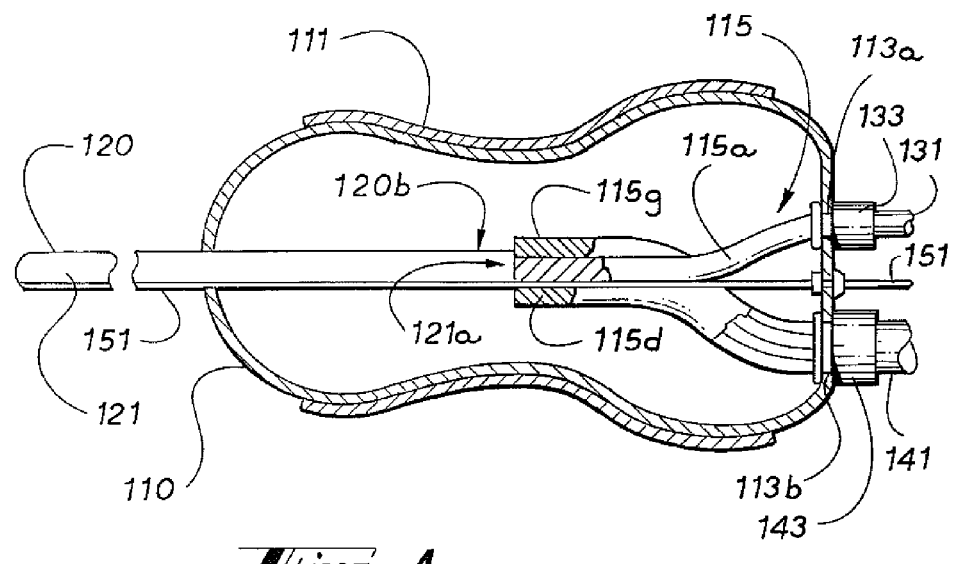
FIG. 4 is an axial-section view of an ophthalmic surgical device according to another alternative configuration.

Now referring more particularly to FIG. 4, each of source waveguides 131 and 141 may optionally include connectors 133 and 143, respectively, at a distal end for removable connection of source waveguides 131, 141 to hand-piece 110 in addition to, or instead of the connectors at the proximal ends. Hand-piece 110 may likewise optionally include connectors 113a, 113b, adapted to securely and removably engage connectors 133 and 143, respectively. Connectors 113a, 113b are preferably spaced from probe 120 such that connectors 133 and 143 are not likely to interfere with physical manipulation or control of probe 120, such as proximate an end of hand-piece 110, as shown in FIG. 4. When source waveguides 131 and 141 are removable from hand-piece 110 via connectors 113a, 113b, 133, and 143, a corresponding number of connector fibers, such as connector fibers 115a-g, are preferably included in optical coupling 115. Connector fibers 115a-g are preferably in operable connection with fiber waveguides 131a and 141b-g at connectors 113a and 113b, and are in operable connection with single-fiber waveguide 121, as described above, at optical coupling 115, i.e. proximal end 121a of single-fiber waveguide 121.

Specifically, each of connector fibers 115a-g is preferably selected to have a cross-sectional area and shape approximately equal to the corresponding one of fiber waveguides of waveguides 131a and 141b-g, and each is preferably connected generally coaxially therewith at connectors 113a, 113b. Thus, the fiber waveguides of optical coupling 115 preferably act as extensions of the fiber waveguides of source waveguides 131 and 141. As a result of such mating of appropriately-sized waveguides, losses of light at connectors 113a, 113b may preferably be reduced or eliminated, such that an amount of light in optical coupling 115 proximate connectors 113a, 113b is preferably substantially equal to an amount of light in source waveguides 131 and 141 proximate connectors 133 and 143.

In use, ophthalmic surgery may be accomplished via selective manipulation of hand-piece 110 to position probe 120 in a desired location, attitude, and orientation for delivery of a treatment, whereby distal end 120a thereof may be disposed proximate a desired surgical site. One or more of laser energy source 130, illumination energy source 140, and accessory 150 may be selectively activated, adjusted, or the like to provide one or more of laser energy, illumination energy, and/or a selected material, chemical, energy, or the like to distal end of probe 120a to effect the ophthalmic surgery or treatment. Preferably, laser energy, when provided by source 130, is transmitted to distal end 121b of single-fiber waveguide 121 via single-fiber waveguide 131a and optical coupling 115. Single-fiber waveguide 121 preferably receives substantially all of the laser energy from single-fiber waveguide 131a, with little or no loss of energy, due to an abutting relationship between single-fiber waveguide 131a and single-fiber waveguide 121, such that the end of single-fiber waveguide 131a is preferably completely covered by single-fiber waveguide 121.

Furthermore, illumination energy, when provided by source 140, is preferably transmitted to distal end 121b of single-fiber waveguide 121 via fiber waveguides 141*b*-*g* of source waveguide 141 and optical coupling 115. Fiber waveguides 141*b*-*g* of source waveguide 141 are preferably disposed generally symmetrically about single-fiber waveguide 131*a*, whereby at least a portion of the illumination energy therewithin may enter single-fiber waveguide 121 via abutting portions of each of fiber waveguides 141*b*-*g* of source waveguide 141 and single-fiber waveguide 121. Additionally, any portion(s) of the end surfaces of fiber waveguides 141*b*-*g* of source waveguide 141 that are not in abutting relationship with an end of single-fiber waveguide 121 may be coupled with another waveguide or optical transmission device, or none at all, and may be directed to an exterior of hand-piece 110, whereby a user may confirm that illumination energy is reaching an interface of single-fiber waveguide 121 and optical coupling 115. Alternatively, however, the laser and/or illumination energies may be transmitted via one or more refractive device, reflective device, optical gel, anti-reflective coating, anti-scattering coating, tapered fiber, fusion bond, weld, combinations thereof, or the like, whereby light loss at the interface may be substantially reduced or eliminated.

A surgical microscope or other visualization tool may be operable with illumination energy source 140, source waveguide 141, optical coupling 115 and single-fiber waveguide 121 to allow illumination energy reflected from the surgical sight to be transmitted to the surgical microscope or other visualization tool, whereby a surgeon or other user of instrument 100 may be able to perceive a present status, characteristic, position, or the like of one or more structure or feature of interest at the surgical site. For example, a surgeon may preferably use a surgical microscope to identify a precise location where application of laser energy is needed to effect a surgery, position probe 121 at the precise location, verify such positioning via the surgical microscope, and deliver an appropriate amount of laser energy to the surgical site.

As will be understood by those ordinarily skilled in the art, a shape, dimension, material, or the like, of each of hand-piece 110, grip 111, and probe 120, may be selected as desired to accommodate user preference, manufacturing considerations, or the like. All such components are, however, preferably formed from inert, hypo-allergenic, durable, and sterile or sterilizable materials, whereby use thereof in an operating or surgical environment is appropriate, and whereby the components may be cleaned, sterilized, or otherwise prepared for subsequent use, including repeated use, or whereby the components may be replaced for subsequent use. Likewise, the dimensions, configurations, materials, or the like, for connectors 113*a*, 113*b*, source waveguides 131 and 141, optical coupling 115, single-fiber waveguide 121, conduit 123, and conduit 151 may be selected to enable proper, adequate, or desired functionality of instrument 100 in effecting a selected surgery. Such dimensions, configurations, materials, or the like, may be selected based on desired or required energy transmission characteristics, fluid flow rates, durability, chemical reactivity, price, workability, or the like, and the cross-sectional dimension of at least single-fiber waveguide 121 and tube 125 is each preferably selected to be as small as possible without substantially adversely affecting the performance characteristics thereof.

Having thus described exemplary embodiments of the present invention, it should be noted by those ordinarily skilled in the art that the within disclosures are exemplary only and that various other alternatives, adaptations, and modifications may be made within the scope and spirit of the present invention. For example, while probe 120 is shown as straight, probe 120 may be formed in other shapes, such as curved, angled, stepped, combinations thereof, or probe 120 may be flexible or adjustable. Similarly, while probe 120, single-fiber waveguide 121, conduit 123, conduit 151, source waveguides 131, 141, and fiber waveguides 131*a*, 141*b*-*g* are shown as round, other shapes may be utilized to accomplish the functions described herein. Accordingly, the present invention is not limited to the specific embodiments as illustrated herein, but is only limited by the following claims.

What is claimed is at least:

1. A waveguide ophthalmic surgical instrument comprising:
    an optical coupling for receiving a surgical laser energy input from a surgical laser energy source and an illumination energy input from an illumination energy source, said optical coupling comprising a centrally disposed first waveguide, wherein said centrally disposed first waveguide is operable with a waveguide associated with the surgical laser energy source, said optical coupling further comprising at least one second waveguide disposed approximately concentrically about said centrally disposed first waveguide, wherein said at least one second waveguide is operable with a plurality of waveguides associated with the illumination energy source; and
    a single-fiber waveguide disposed within a probe carried by a handpiece of said waveguide ophthalmic surgical instrument, wherein said single-fiber waveguide is operable with said centrally disposed first waveguide of said optical coupling proximate a cross-sectional center of said single-fiber waveguide, such that surgical laser energy may be transmitted approximately centrally through said single-fiber waveguide; wherein said single-fiber waveguide is further operable with but a portion of said at least one second waveguide of said optical coupling disposed adjacent a peripheral margin of said single-fiber waveguide, such that illumination energy may be transmitted through said single-fiber waveguide in a manner that does not interfere with transmission of surgical laser energy; and wherein the cross-sectional area of said single-fiber waveguide is less than the combined cross-sectional areas of said centrally disposed first waveguide and said at least one second waveguide of said optical coupling,
    wherein said optical coupling is operable to transmit surgical laser energy from the surgical laser energy source and illumination energy from the illumination energy source within said single-fiber waveguide for combined delivery thereof to a surgical site proximate a distal end of said single-fiber waveguide.

2. The waveguide ophthalmic surgical instrument of claim 1, wherein said optical coupling further comprises at least one of an optical gel, an anti-reflective coating, an anti-scattering coating, a reflective element, a refractive element, a tapered fiber, a fusion bond, and a weld.

3. The waveguide ophthalmic surgical instrument of claim 1, wherein said probe further comprises a conduit, said conduit providing access to the surgical site proximate a distal end of conduit.

4. The waveguide ophthalmic surgical instrument of claim 3, wherein said probe comprises a tube.

5. The waveguide ophthalmic surgical instrument of claim 4, wherein said tube comprises an aperture through a sidewall thereof for passage of material, said aperture allowing passage of the material without interfering with transmission of laser or illumination energy proximate said optical coupling.

6. The waveguide ophthalmic surgical instrument of claim 1, further comprising a coupler for retaining said single-fiber waveguide in operable communication with a plurality of fiber waveguides of said optical coupling.

7. A method of effecting a surgery using the waveguide ophthalmic surgical instrument of claim 1, comprising the steps of:
disposing a distal end of said single-fiber waveguide of said instrument proximate an intraocular surgical site via manipulation of said instrument; and
supplying a first laser energy to said optical coupling of said instrument via a first connector;
supplying a second illumination energy to said optical coupling of said instrument via a second connector, said second illumination energy being supplied from a source separate from a source of said first laser energy; and
delivering said first laser energy and said second illumination energy to the intraocular surgical site via said single-fiber waveguide,
wherein delivery of at least one of said laser light energy and said second illumination energy enables said surgery.

8. The method of claim 7, further comprising the step of at least one of selectively controlling and selectively adjusting said source of said laser energy to deliver a predetermined amount of said laser energy to said surgical site.

9. The method of claim 7, further comprising the step of at least one of selectively controlling and selectively adjusting said source of said illumination energy to deliver a predetermined amount of said illumination energy to said surgical site.

10. The method of claim 7, wherein said optical coupling is retained in operable communication with said single-fiber waveguide via a coupler.

11. The method of claim 7, further comprising at least one of the step of delivering a selected material to the surgical site via a conduit of said instrument and the step of removing a selected material from the surgical site via said conduit of said instrument.

12. The method of claim 11, wherein at least one of the step of delivering a selected material to the surgical site via a conduit of said instrument and the step of removing a selected material from the surgical site via said conduit of said instrument is accomplished via an accessory operable with said conduit.

13. The method of claim 7, further comprising the step of detecting a parameter via a conduit of said instrument.

14. An ophthalmic surgical device comprising:
a single-fiber waveguide disposed within a probe carried by a handpiece;
an optical coupling operable with said single-fiber waveguide, said optical coupling comprising a centrally disposed surgical laser energy waveguide, said centrally disposed surgical laser energy waveguide optically communicating with a waveguide associated with a surgical laser energy source, said optical coupling further comprising a plurality of illumination energy waveguides disposed approximately concentrically about said centrally disposed surgical laser energy waveguide, each of said plurality of illumination energy waveguides optically communicating with a corresponding one of a plurality of waveguides associated with an illumination energy source;
said single-fiber waveguide optically communicating with said centrally disposed surgical laser energy waveguide of said optical coupling proximate a cross-sectional center of said single-fiber waveguide, such that surgical laser energy may be transmitted approximately centrally through said single-fiber waveguide; said single-fiber waveguide further optically communicating with but a portion of each of said plurality of illumination energy waveguides of said optical coupling disposed adjacent a peripheral margin of said single-fiber waveguide, such that illumination energy may be transmitted through said single-fiber waveguide in a manner not interfering with transmission of surgical laser energy; and wherein the cross-sectional area of said single-fiber waveguide is less than the combined cross-sectional areas of said centrally disposed surgical laser energy waveguide and said plurality of illumination energy waveguides of said optical coupling;
wherein said single-fiber waveguide disposed within said probe is enabled to transmit surgical laser energy from the surgical laser energy source to an intraocular surgical site, and is further enabled to transmit illumination energy from the illumination energy source to illuminate the intraocular surgical site.

15. The ophthalmic surgical device of claim 14, wherein said probe comprises a tube and a space between said tube and said single-fiber waveguide disposed within said probe.

16. The ophthalmic surgical device of claim 14, further comprising a coupler for retaining said one single-fiber waveguide disposed within said probe in operable connection with said plurality of fiber waveguides of said optical coupling.

* * * * *